(12) United States Patent
Freyman et al.

(10) Patent No.: US 7,758,587 B2
(45) Date of Patent: Jul. 20, 2010

(54) MEDICAL DEVICE GUIDANCE FROM AN ANATOMICAL REFERENCE

(75) Inventors: Toby Freyman, Waltham, MA (US); Timothy J. Mickley, Elk River, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1323 days.

(21) Appl. No.: 10/680,288

(22) Filed: Oct. 8, 2003

(65) Prior Publication Data

US 2005/0080429 A1    Apr. 14, 2005

(51) Int. Cl.
*A61F 4/00*    (2006.01)
(52) U.S. Cl. .............................. 606/108; 606/1; 600/424
(58) Field of Classification Search ...................... 606/1, 606/108; 600/117, 145, 424, 139
See application file for complete search history.

(56) References Cited

U.S. PATENT DOCUMENTS

| | | | | |
|---|---|---|---|---|
| 4,254,649 A | * | 3/1981 | Cervenka et al. ............... | 72/128 |
| 4,410,320 A | * | 10/1983 | Dykstra et al. ............... | 604/270 |
| 4,690,673 A | * | 9/1987 | Bloomquist ................. | 604/67 |
| 5,199,950 A | | 4/1993 | Schmitt et al. | |
| 5,228,441 A | * | 7/1993 | Lundquist ................... | 600/380 |
| 5,448,989 A | * | 9/1995 | Heckele ...................... | 600/142 |
| 5,628,777 A | * | 5/1997 | Moberg et al. ............... | 607/122 |
| 5,693,043 A | * | 12/1997 | Kittrell et al. ................. | 606/15 |
| 6,171,253 B1 | * | 1/2001 | Bullister et al. ............. | 600/486 |
| 6,272,371 B1 | * | 8/2001 | Shlomo ...................... | 600/424 |
| 6,323,459 B1 | | 11/2001 | Maynard | |
| 6,540,670 B1 | * | 4/2003 | Hirata et al. ................. | 600/152 |

FOREIGN PATENT DOCUMENTS

WO        9729682        8/1997

* cited by examiner

*Primary Examiner*—Michael J Milano
*Assistant Examiner*—Victor X Nguyen
(74) *Attorney, Agent, or Firm*—Crompton, Seager & Tufte, LLC

(57) ABSTRACT

A system and method for simply and reliably determining the location and orientation of a medical device within a patient's body. A medical device, such as a catheter, has bending indicators on or imbedded in its wall, and passes through an anatomical reference of known orientation relative to a target site within the patient. Information from the tube bending indicators permits determination of the orientation of a feature, such as an orifice, at the distal end of the medical device relative to the anatomical reference. From the known orientation of the anatomical reference, and information on the location and orientation of the distal end of the medical device obtained from fluoroscopic imaging from a single direction, the physician may reliably determine the orientation of the distal feature relative to the target site, eliminating the need for imaging from multiple directions.

14 Claims, 8 Drawing Sheets

MEDICAL DEVICE GUIDANCE FROM AN ANATOMICAL REFERENCE

FIELD OF THE INVENTION

The present invention is directed to the field of guidance for medical device deployment and use within the body of a patient.

BACKGROUND

Medical catheters, guide catheters and guide tubes are used for innumerable minimally-invasive medical procedures, wherein a tube is inserted into a lumen in a patient's body, such as a blood vessel, and maneuvered to a target site, such as a heart chamber or another blood vessel. These catheters and guide tubes may be used as conduits for a variety of medical procedures, including delivery of therapeutic drug doses to target tissues, delivery of medical devices such as lumen-reinforcing or drug-eluting stents, and guiding medical instruments to a target site to perform a surgical procedure, such as tissue rescission, ablation of obstructive deposits or myocardial revascularization.

In order to accurately maneuver a catheter or similar medical device (such as a guide tube or a guide wire) through a body lumen to a target site, means of ascertaining the location and orientation of the device are needed. A frequently used imaging technique employs fluoroscopy to image the device.

Maneuvering and placement of medical devices such as catheters frequently requires imaging from multiple angles or with multiple imaging devices. This is necessary in order to obtain an adequate image of the target site and the device, and to verify that the device is oriented in the desired direction, i.e., to verify that the tube is not, for example, rotated into a position which appears to be correct when viewed by fluoroscopy from one direction, but is in fact rotated about a plane of imaging away from the desired orientation, e.g., positioned away from instead of toward the imaging equipment, or vice-versa. The need for multiple views of the device increases the complication, time and expense of a medical procedure, as either multiple fluoroscopes must be employed to obtain the desired views, or a single fluoroscope must be sequentially set up, used, repositioned, etc. to provide adequate imaging coverage. Alternative imaging techniques that may provide higher resolution in the future have demonstrated some potential (such as MRI-based catheter imaging techniques); however, such developments have not as yet advanced to the point of regular clinical use or undesirably add cost, large, bulky equipment and/or additional imaging set-up and use time to the overall procedure.

Thus, there is a need for a simplified, reliable method and system for guiding medical devices such as catheters to a target site within a patient and ensuring the distal end of such devices are properly located and oriented at a target site.

SUMMARY OF THE INVENTION

Embodiments of the present invention may include a method and system for overcoming one or more of the foregoing disadvantages. Generally, embodiments of the present invention may be directed to a medical device, such as a catheter, guide tube, guide wire, etc., that can traverse a lumen within a patient's body and may be equipped with a plurality of device bending indicators. When the portion of the device with the bending indicators (the reference portion) is located within a known anatomical reference plane, the bending indicators provide an operator with an indication of the orientation of the device.

In one embodiment, there may be a guide catheter with a bend at its distal end such that its distal orifice is located at an angle with respect to the longitudinal axis of the catheter, through which a medical instrument, such as a percutaneous myocardial revascularization laser may be operated. This catheter is equipped with strain gauges along its wall, which measure localized stresses in the wall as the tube bends along a curved path. The stress indications provided by the strain gauges provide an indication of the bending of the catheter, for example, indicating which portion of the catheter is at the inside of the curve, and which portion is at the outside of the curve. If the strain gauges are located at a portion of the catheter which is bent as it passes through an anatomic reference geometry or region with a known configuration (an "anatomical reference"), such as through the aorta arch as the catheter passes though the aorta on the way to the left ventricle, the orientation of the distal catheter orifice may be simply and reliably determined. This information, combined with information obtained from fluoroscopic imaging from a single direction and knowledge of the orientation of the anatomical reference relative to the target site, permits a physician to efficiently and reliably determine whether the medical device is properly positioned and oriented with respect to the target site.

Specifically, when the catheter passes through the anatomical reference plane and a bend in the catheter is formed, the strain gauges provide information on the direction in which the reference portion of the catheter is bent. Thus, this provides an indication of the relative rotation of the catheter with respect to the known anatomical reference. Because the orientation of a feature of the catheter such as a distal orifice relative to the strain gauges is also known, this information in turn provides an indication of the orientation of the distal orifice relative to the anatomical reference. When the information on the location and orientation of the distal end of the catheter obtained from the fluoroscopic imaging is combined with information on the orientation of the distal orifice relative to the reference, an unambiguous determination of the position and orientation of the distal orifice may be obtained. Any desired position and/or orientation corrections may then be made to ensure the medical device is properly oriented with respect to the target site, and the procedure then commenced.

The foregoing method and system is amenable to a number of variations. For example, the strain gauges may be located within the wall of the catheter, or may be placed on a catheter wall surface, including either the inner or the outer surfaces of the catheter. Other wall bending indicators may also be employed, such as longitudinal rods contained within the catheter wall and emerging at the proximal end of the catheter wall, wherein as the catheter is curved as it passes through the anatomical reference, the rod(s) at the inside radius of the bend protrude farther from the proximal end of the catheter than the rod(s) at the outside radius of the bend. The distal end of the catheter may also comprise a variety of configurations, including, in addition to the foregoing transverse orifice, an angled distal tip whose longitudinal axis is displaced from the longitudinal axis of the catheter.

Because the present invention permits rapid, reliable determination of the position and orientation of medical devices with minimal imaging equipment and procedural complication, proper placement of minimally-invasive medical devices may be reliably achieved in less time and at a lower cost. These benefits may permit a reduced length of time the patient must be under anesthesia or subjected to radiation from fluoroscopy, thus increasing patient safety and lowering costs due to decreased demand for physician, supporting personnel and operating facility time for each procedure, and minimized capital equipment and operating costs due to decreased imaging equipment requirements.

BRIEF DESCRIPTION OF THE DRAWINGS

The foregoing and further features and advantages of the present invention will become apparent from the following description of preferred embodiments with reference to the accompanying drawings, wherein like numerals are used to represent like elements and wherein.

DETAILED DESCRIPTION

Figure 1:
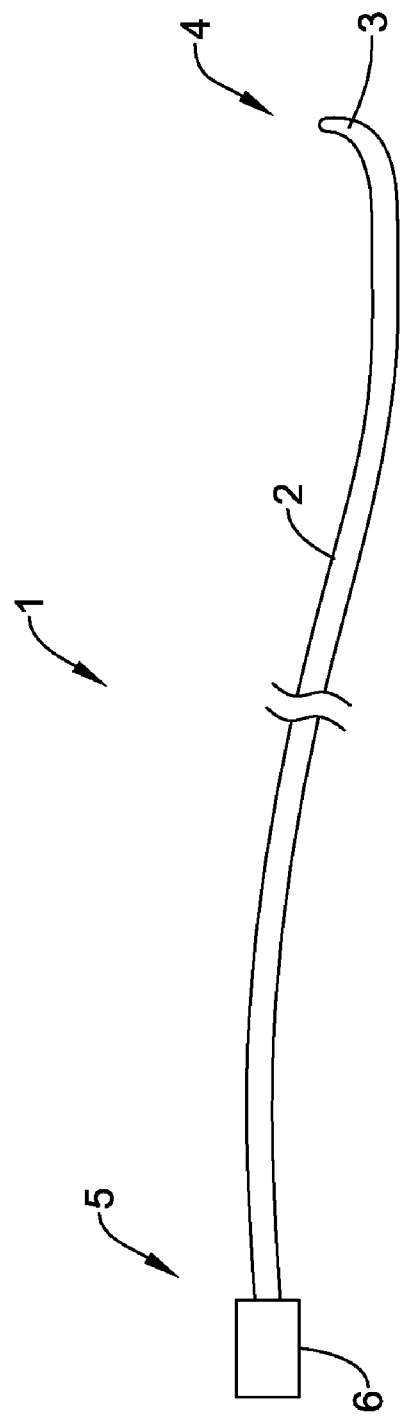
FIG. 1 is an illustration of a catheter in accordance with an embodiment of the present invention.

FIG. 1 illustrates a catheter 1 in accordance with an embodiment of the present invention. Catheter 1 comprises a tube 2 forming a lumen 8 therein (shown in FIG. 2), with a distal orifice 3 formed at a distal end 4 of catheter 1. At a proximal end 5 of catheter 1 are fittings for use of the catheter, illustrated schematically by terminal box 6, including, for example, means for guiding and manipulating the catheter toward a target site, provisions for passage of fluids and/or other medical devices through lumen 8 to a target site via distal orifice 3, and connections for reading instrumentation contained on or within catheter 1. Catheter 1 may be formed from materials and processes well known in the catheter manufacture art.

Figure 2B:
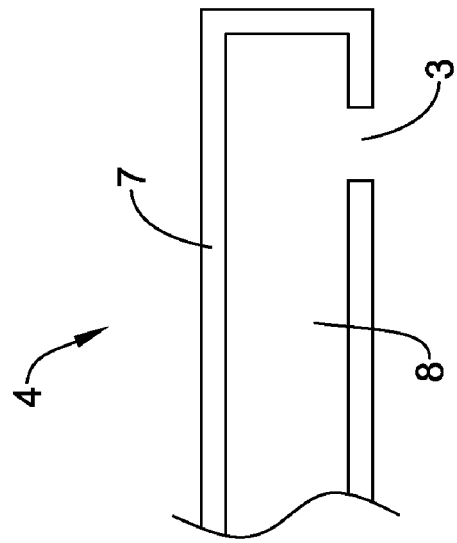
FIG. 2b is a cross-section illustration of a transverse distal catheter orifice in accordance with another embodiment of the present invention.
Figure 2A:
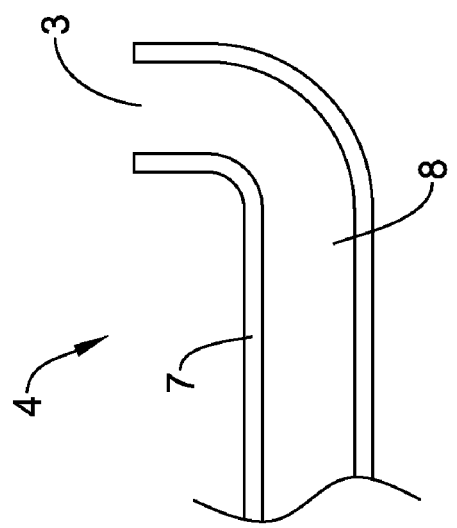
FIG. 2a is a cross-section illustration of an angled distal catheter orifice in accordance with an embodiment of the present invention.

FIG. 2a illustrates the configuration of distal end 4 in the present embodiment. FIG. 2a is a longitudinal cross-section view of catheter 1 showing tube wall 7 and the lumen 8 formed therein. Catheter 1 may alternatively include multiple lumens; however, only lumen 8 is illustrated in the present embodiment for simplicity. In this embodiment, distal orifice 3 is located at the end of an angled tip whose longitudinal axis is displaced at an angle from the longitudinal axis of catheter 1. Such an angled tip may be employed, for example, in a procedure where there is not enough space to maneuver the distal end of the catheter to align its longitudinal axis with the target site. FIG. 2b illustrates an alternative distal orifice configuration, where orifice 3 is located in catheter wall 7 near distal end 4, and communicates with lumen 8.

Figure 3:
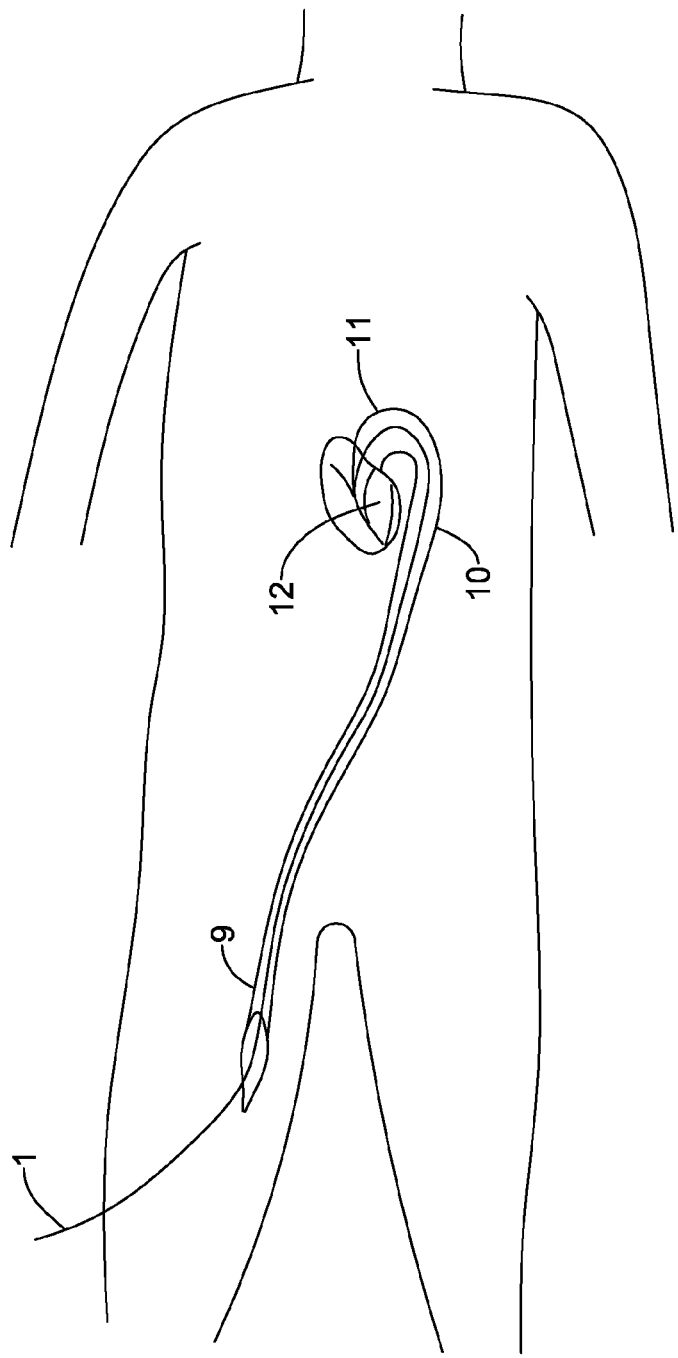
FIG. 3 is a schematic illustration of the routing of a catheter through a blood vessel to the left ventricle of a patient's heart through the aortic arch in accordance with an embodiment of the present invention.
Figure 4:
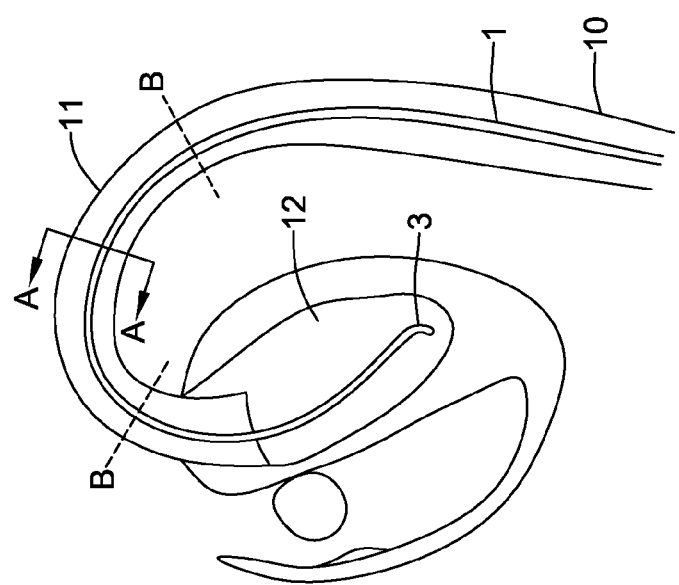
FIG. 4 is more detailed illustration of the placement of a catheter within the left ventricle of the heart and the bending of the catheter as it passes through the aortic arch in accordance with an embodiment of the present invention.

The embodiment shown in FIGS. 3 and 4 includes the use of a catheter to perform a minimally invasive medical procedure in the left ventricle of a patient's heart. As illustrated in FIG. 3, catheter 1 is inserted by the physician into an artery in a location that permits effective control of the catheter as it is maneuvered toward the heart, in this case through femoral artery 9. Catheter 1 may be maneuvered through the femoral artery to and through the descending aorta 10 and aortic arch 11, and then into left ventricle 12 until distal orifice 3 is located in the vicinity of a target site within the heart. FIG. 4 provides a view of distal end of the catheter within left ventricle 12, and illustrates a portion of aortic arch 11 (denoted by dashed lines B-B) which defines an anatomical reference geometry. Catheter 1 curves through this anatomical reference as it travels from descending aorta 10 to left ventricle 12.

Figure 5:
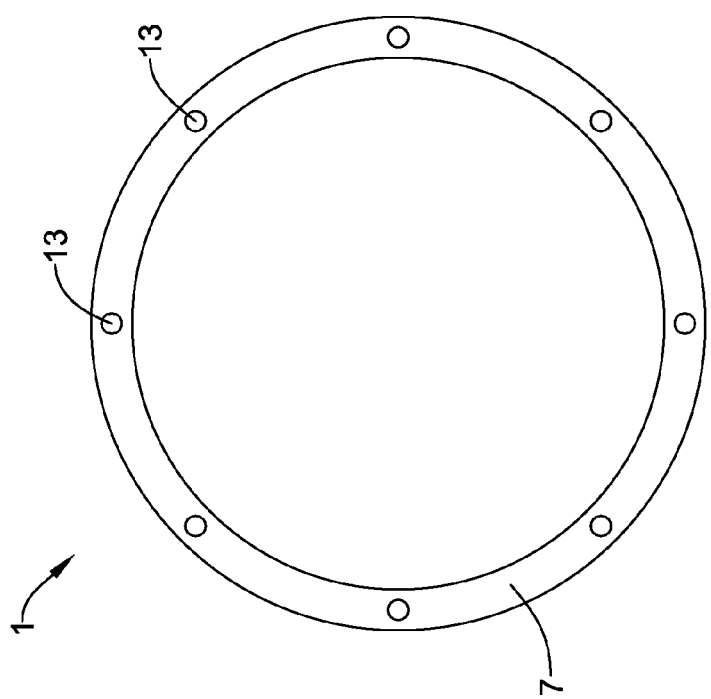
FIG. 5 is a transverse cross-section view of a portion of the catheter within the aortic arch at Section A-A shown in FIG. 4 in accordance with an embodiment of the present invention.
Figure 6:
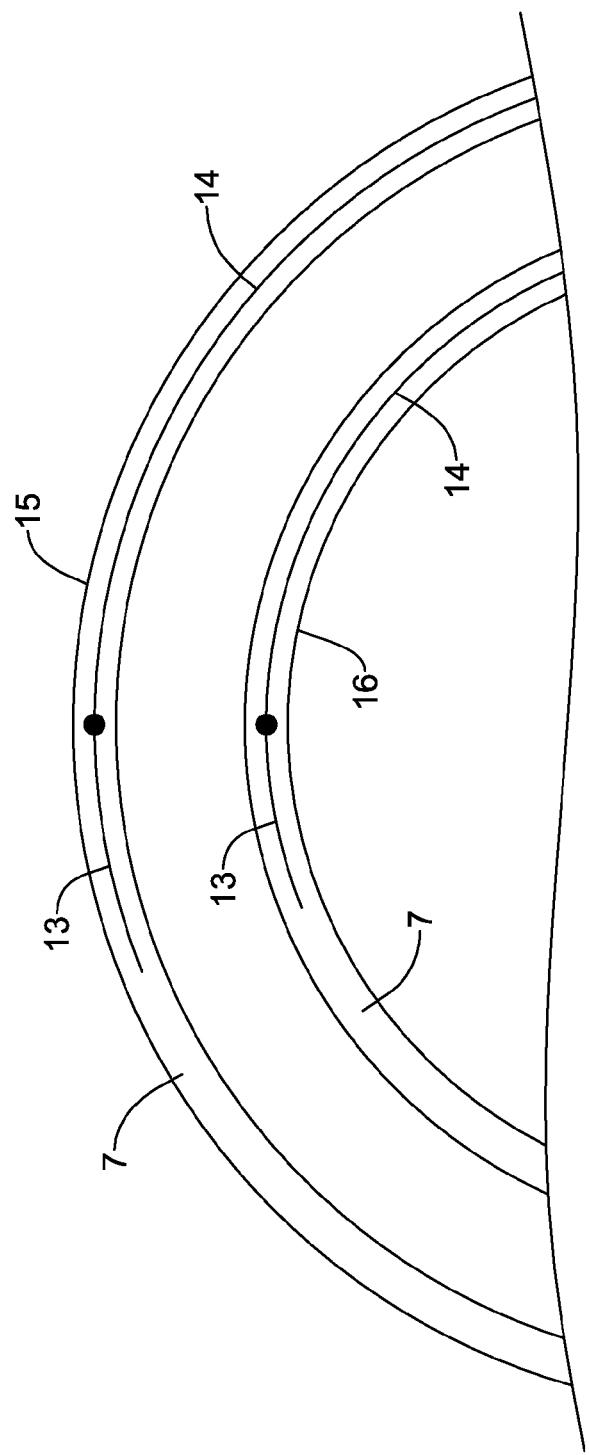
FIG. 6 is a longitudinal cross-section view of a portion of the catheter within the aortic arch in accordance with an embodiment of the present invention.

Catheter 1 is equipped with wall bending indicators within catheter wall 7 in the reference portion of the catheter, i.e., the portion of the catheter that is located within aortic arch 11 when catheter distal end 4 is in the vicinity of the target site. These bending indicators provide an indication of the amount of localized bending, i.e., localized compressive or tensile stress, in the portion of tube wall immediately adjacent to each stress indicator. As shown in FIG. 5 and 6, in this embodiment catheter 1 contains eight bending indicators 13 that may be evenly spaced about the circumference of the catheter within catheter wall 7, in a known relationship. In the present embodiment, bending indicators 13 may be strain gauges of a conventional type arranged in catheter wall 7 parallel to the longitudinal axis of catheter 1. The strain gauges may provide an indication of the magnitude of the tensile or compressive stress in the portion of catheter wall 7 adjacent to each gauge by changing their internal resistance as the portion of the tube wall monitored by each gauge is elongated or shortened (corresponding to the application of tensile or compressive stresses, respectively, on catheter wall 7 as the tube wall bends where it passes through the anatomical reference).

The eight strain gauges located within catheter wall 7 are connected via signal wires 14 which run through catheter wall 7 to catheter proximal end 5, and may be connected to resistance monitoring equipment (not illustrated) which provides the physician a convenient display identifying, for example, the strain gauges with the highest and lowest stress levels (corresponding to the outer and inner radii of the curve), or the orientation of the distal end of the catheter. The strain gauges may be located on the inner or outer surface of catheter wall 7 instead of imbedded within the wall, and signal wires 14 may be permitted to remain outside the inner or outer wall surfaces.

Once catheter 1 is maneuvered to the target site, each of the strain gages may be monitored to determine the relative tube wall stress in the wall in the portion of the catheter within the anatomical reference plane. Due to the curvature of catheter 1 as it passes through the aortic arch, the strain gage at the outer radius of the curve 15 will indicate the greatest tensile stress in the wall, and the strain gage closest to the inside radius of the curve 16 will indicate a local wall stress that will be either compressive or tensile. If the stress at the inner radius is tensile, it will be lower in magnitude than the wall stress at the outer radius.

The indication of which portions of the catheter are located at the outer and inner radii of the aortic arch permits the determination of the orientation of distal orifice 3 relative to the aortic arch. The location of each strain gauge about the circumference of catheter 1 is known, and the orientation of the distal orifice of the catheter relative to the locations of the strain gauges is known. From the strain gauge indications of catheter wall stress (observable, for example, on a display on monitoring equipment receiving the signals from the strain gauges via signal wires 14), it may be determined which of the strain gauges is located closest to outer radius 15 (i.e., the strain gauge indicating the greatest tensile stress) and which strain gauge is located closest to inner radius 16 (i.e., the strain gauge indicating the greatest compressing stress or, in the absence of any gauge indicating compressive stress, the lowest tensile stress). Then, because the orientation of the strain gauge is known, and the orientation of distal orifice 3 relative to the strain gauges is also known, the orientation of distal orifice 3 relative to the anatomical reference (through which the guide tube curves) may be ascertained. For example, in the present embodiment, the strain gauge wall stress indications will reveal the direction in which distal orifice 3 is pointing relative to the aortic arch (e.g., 30 degrees posterior to the plane of the arch, 135 degrees anterior to the plane, or within the plane of the arch).

Next, taking information obtained from a fluoroscopic image of the target site identifying the orientation and location of catheter distal end 4, information obtained from the strain gages as to the orientation of distal orifice 3 relative to the anatomical reference, knowledge of the fixed relationship between the anatomical reference and the target site (in this embodiment, aortic arch 11 and left ventricle 12), and knowledge of the fixed relationship between distal end 4 and distal orifice 3, a physician may determine whether distal orifice 3 is located at, and oriented toward, the target site in a desired manner. For example, while the fluoroscopic image may identify the location and general orientation of distal end 4 at the target site, this single image may leave some ambiguity as to the orientation of distal orifice 3 (e.g., whether rotated toward the anterior or posterior directions); however, the information provided by the bending indicators (strain gages) in the anatomical reference plane will unambiguously identify the orientation of distal orifice 3 on distal end 4, and thus the orientation of distal orifice 3 relative to the target site. Unambiguous determination of the orientation and location of the medical device therefore may be reliably assured without the need for additional fluoroscopic imaging from more than one direction, i.e., without the need for expensive additional imaging equipment or time-consuming re-positioning of a single fluoroscopic imaging unit in order to obtain images from multiple directions.

As will be readily understood by those of ordinary skill, the location and orientation of the aortic arch relative to the left ventricle of the heart is generally well-defined and, while not precisely identical between patients, is sufficiently anatomically consistent to permit the use of the aortic arch as a reference for guidance of catheter 1 of the present embodiment. Those of ordinary skill also will recognize that the anatomical reference need not define a precisely two-dimensional planar surface, but instead need only define a generally predictable curve through which the catheter must pass with significant curvature in order to use the present system and method.

The foregoing embodiment is directed to location and orientation of a catheter within the left ventricle of the heart. Those of ordinary skill in the art will readily recognize that the present invention is not limited to use in coronary procedures, nor limited to the passage of catheters through a patient's vasculature. Rather, this invention may be employed in any procedure that requires the routing of a tube or wire through a bodily lumen, such as a urinary tract, where the device must curve as it passes through a known anatomical reference, such as the aortic arch in the preceding example.

Figure 7A:
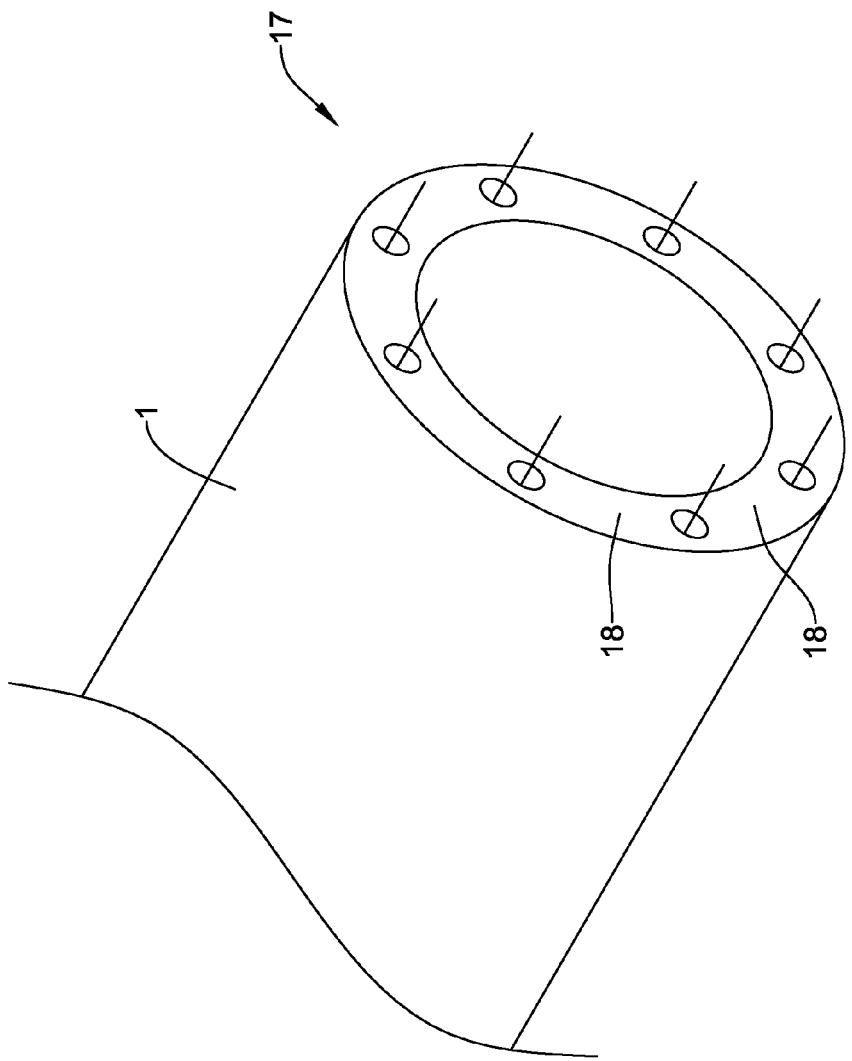
FIG. 7a is an illustration of a proximal end of a catheter illustrating alternative catheter wall bending indicators in accordance with a second embodiment of the present invention.
Figure 7B:
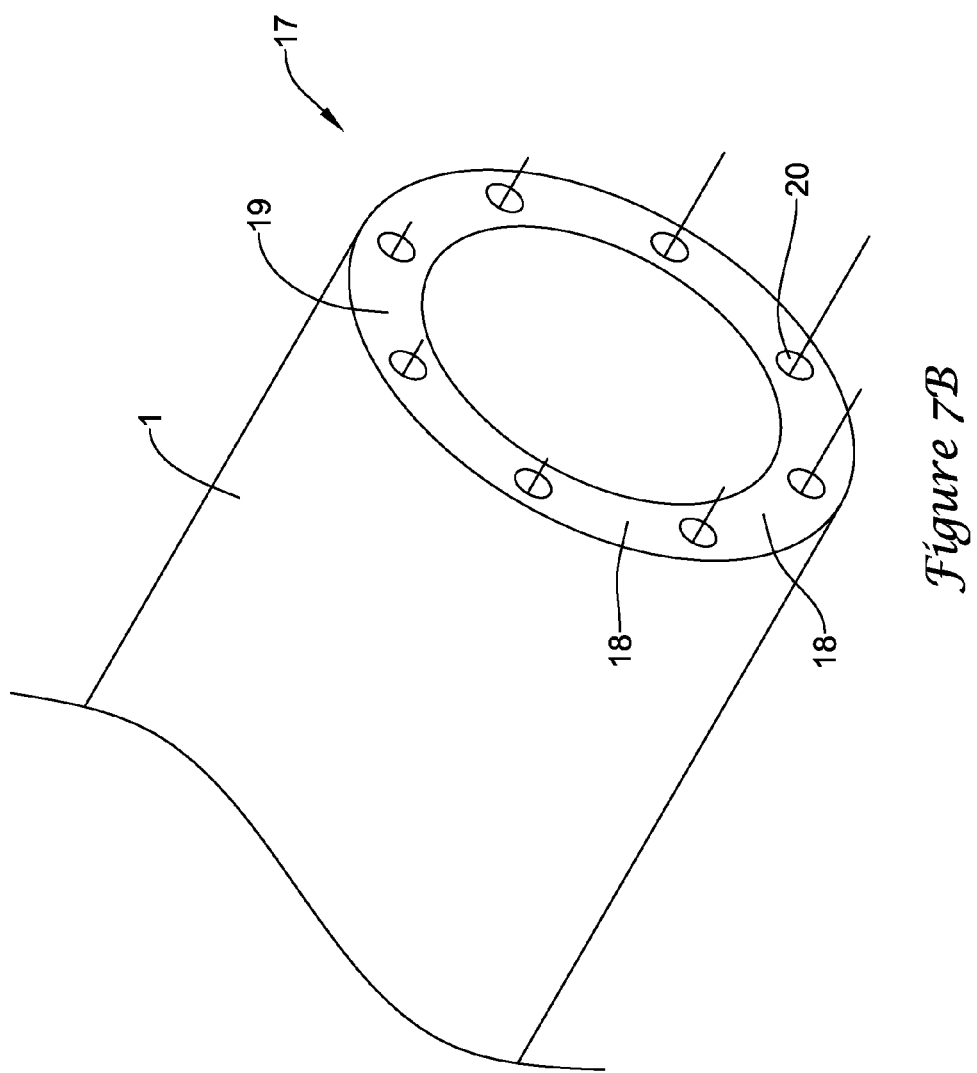
FIG. 7b is an illustration of a proximal end of the catheter in FIG. 7a illustrating catheter wall bending indications provided when the catheter is curved in accordance with a second embodiment of the present invention.

In an alternative embodiment of the present invention, rather than strain gages that provide an indication of localized wall stress when catheter 1 is curved, the wall bending indicators may be elongated rods that pass from the region of curvature in the anatomical reference to an indicator panel at the proximal end of the catheter, as illustrated in FIGS. 7a and 7b. The distal ends of the elongated rods may be held in place within catheter 1 by, for example, frictional engagement with the catheter wall. The remaining portions of the elongated rods, however, must be free move longitudinally within the wall of the catheter all the way from the region of the catheter located within the anatomical reference to the proximal end of catheter, for reasons that will be further explained below.

FIG. 7a illustrates the proximal end of catheter 1, from which indications of tube wall bending may be obtained when catheter 1 curves through the anatomical reference. Alternatively, rather than being located directly at the proximal end of catheter 1, the indicator panel 17 illustrated in FIG. 7a may be located at a proximal end of a side tube emerging from the side of the proximal end of catheter 1 through which the proximal ends of the elongated tubes are routed. This alternative configuration would permit the proximal ends of the wall bending indicator rods to be located away from the proximal end of the catheter lumen, thereby avoiding unnecessary interference with the performance of the medical procedure through the catheter lumen.

As shown in FIG. 7a, when catheter 1 is in an initial rest position, wherein the portion of the catheter that will be positioned within the anatomical reference plane is not yet curved, the proximal ends of elongated rods 18 may be arranged such that all of the rods extend from the face of indicator panel 17 approximately the same distance.

FIG. 7b illustrates the indicator panel of FIG. 7a following placement of catheter 1 within the patient, such that the catheter is curved as it traverses the anatomical reference, as illustrated in FIG. 4. As catheter 1 curves around the anatomical reference, the outer radius of the catheter is placed under tension. This tension generates a strain, i.e., an increase in length due to an applied tensile force, which elongates the tube wall along the outside radius of the curve. Similarly, at the inner radius of the curve in catheter 1, the tube wall is placed under compression by the bending, or at least faces tension that is lower in magnitude than the tension at the outer radius of the catheter. The catheter wall at the inner radius accordingly either is shortened or, if under tension, is elongated by an amount less than the tube wall at the outer radius. While the catheter wall is being locally elongated or shortened, the overall lengths of the elongated rods 18 are not changing. Because the distal ends of elongated rods 18 are fixed at their distal ends to the catheter wall, as the tube wall is locally elongated or shortened, the remaining portions of the elongated rods 18 are able to move longitudinally relative to the catheter wall. As a result, as a portion of the tube wall is elongated, the distance by which the elongated rod 18 associated with this portion of the tube wall extends beyond indicator panel face 17 decreases relative to an initial rest position. Conversely, as the tube wall is subjected to compressive stresses, thereby shortening the tube wall, the elongated rod 18 in the vicinity of the compressed portion of the tube wall extends farther from the indicator panel face 17 as compared to its initial rest position.

In this embodiment, the portion of the catheter wall closest to the outer radius of catheter 1 will be subjected to the greatest tensile stress in catheter 1, and therefore the elongated rod 18 closest to the outer radius (identified in FIG. 7b as emerging from rod lumen 19) will appear at indicator panel 17 to extend the least distance beyond the face of the panel relative to the remaining elongated rods 18. Conversely, the portion of the catheter wall closest to the inner radius of catheter 1 will be subjected to the greatest compressive (or alternatively, least tensile) stress in catheter 1, and therefore the elongated rod 18 closest to the inner radius (identified in FIG. 7b as emerging from rod lumen 20) will appear at indicator panel 17 to extend the farthest distance beyond the face of the panel relative to the remaining elongated rods 18. Thus, from the relative displacement of elongated rods 18 from their respective initial rest positions at indicator panel 17, a physician may readily determine which portion of the catheter is at the outer radius of the anatomical reference, and thus, as in the first embodiment, determine the relative orientation of the reference portion of the tube and distal orifice 3.

While the present invention has been described with reference to what are presently considered to be preferred embodiments thereof, it is to be understood that the present invention is not limited to the disclosed embodiments or constructions. On the contrary, the present invention is intended to cover various modifications and equivalent arrangements. In addition, while the various elements of the disclosed invention are described and/or shown in various combinations and configurations, which are exemplary, other combinations and configurations, including more, less or only a single embodiment, are also within the spirit and scope of the present invention.

What is claimed is:

1. An apparatus for determining the orientation of a medical device within a patient's body, comprising:
    a catheter having a tube wall defining a lumen therethrough, wherein the catheter is radiopaque under x-ray fluoroscopy; and
    a plurality of tube wall bending indicators located at least on or within the catheter wall at a reference portion of the catheter to become curved where the catheter passes through an anatomical reference when the distal end of the catheter is at a target site within the patient's body;
    wherein the plurality of tube wall bending indicators provide an indication of tube wall bending to indicate the orientation of the reference portion of the catheter relative to the anatomical reference;
    wherein the tube wall bending indicators comprises: a plurality of strain gauges for providing said indication of tube wall bending by changing an electrical resistance in accordance with an amount of tube wall bending within the vicinity of each strain gauge.

2. The apparatus of claim 1, wherein the catheter further comprises:
    a distal outlet in communication with the lumen, and wherein the tube wall bending indicators provide an indication of the orientation of the catheter distal outlet.

3. The apparatus of claim 1, further comprising an orientation display to display an indication of the orientation of the reference portion of the catheter relative to the anatomical reference based on the electrical resistance change of the strain gauges.

4. The apparatus of claim 3, further comprising signal wires linking each of the plurality of strain gauges to the orientation display, and wherein the electrical resistance changes in the strain gauges are transmitted to the orientation display via the signal wires.

5. The apparatus of claim 1, wherein the tube wall bending indicators comprise:
    a plurality of rods movably embedded in the catheter wall, wherein each of the rods extends from a proximal end of the catheter to at least the reference portion of the catheter that becomes curved when the catheter is placed at the target site, the rods to provide said indication of tube wall bending by changing an amount of protrusion relative to the proximal end of the catheter in accordance with an amount of tube wall bending in the vicinity of each rod.

6. The apparatus of claim 1, wherein the strain gauges are located within the catheter wall.

7. The apparatus of claim 1, wherein bending of the tube wall imparts tensile or compressive stress on one or more of the bending indicators.

8. The apparatus of claim 1, wherein the bending indicators comprise:
    a plurality of rods longitudinally disposed within the tube wall, wherein each of the rods are free to move longitudinally relative to the tube wall, and wherein each of the rods extends from a proximal end of the catheter to at least the reference portion of the catheter.

9. The apparatus of claim 8, wherein the distal ends of the rods are fixed to the tube wall.

10. The apparatus of claim 8, wherein each of the rods protrudes from the proximal end of the catheter, and wherein the amount of protrusion of each rod varies according to the amount of tube wall bending in the vicinity of each rod.

11. The apparatus of claim 8, further comprising a panel at a proximal portion of the catheter, wherein the proximal ends of the rods emerge from the face of the panel.

12. The apparatus of claim 11, wherein the panel is located on the proximal end of the catheter.

13. The apparatus of claim 11, further comprising a side tube connected to a proximal portion of the catheter, wherein the rods are routed through the side tube, and wherein the panel is located on the side tube.

14. The apparatus of claim 11, wherein all the rods extend from the face of the panel approximately the same distance when the catheter is in an unbended configuration.

* * * * *